United States Patent [19]

Smith

[11] 4,315,592
[45] Feb. 16, 1982

[54] DISPOSABLE RECEPTABLE FOR EXPENDABLE ITEM

[76] Inventor: Daniel L. Smith, 943 Oak Springs Court, Stone Mountain, Ga. 30083

[21] Appl. No.: 188,324
[22] Filed: Sep. 18, 1980
[51] Int. Cl.³ .......................... B65D 5/10; B65D 85/00
[52] U.S. Cl. ...................................... 229/38; 206/366; 206/370; 206/491; 229/39 R
[58] Field of Search ............... 206/370, 366, 363, 491; 229/38, 39 R

[56] References Cited

U.S. PATENT DOCUMENTS

| | | | |
|---|---|---|---|
| 1,603,024 | 10/1926 | Childs | 229/38 |
| 3,226,007 | 12/1965 | Thies et al. | 229/39 R |
| 4,121,755 | 10/1978 | Meseke et al. | 206/366 |

Primary Examiner—William T. Dixson, Jr.
Attorney, Agent, or Firm—James B. Middleton

[57] ABSTRACT

A receptacle for used expendable hypodermic needles and syringes is disclosed. The receptacle includes a container having baffles as an upper closure, there being two baffles having openings off-set from each other so that items within the container will not be contacted by a person depositing another item into the container. One of the baffles can be moved to a closed position in which it closes the openings to seal off the container, and a tab locks the baffle in the closed position.

6 Claims, 6 Drawing Figures

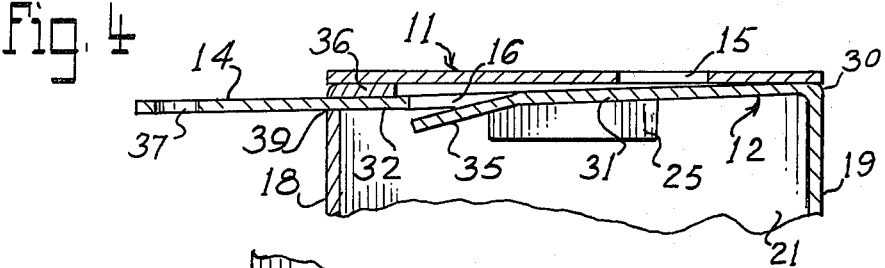
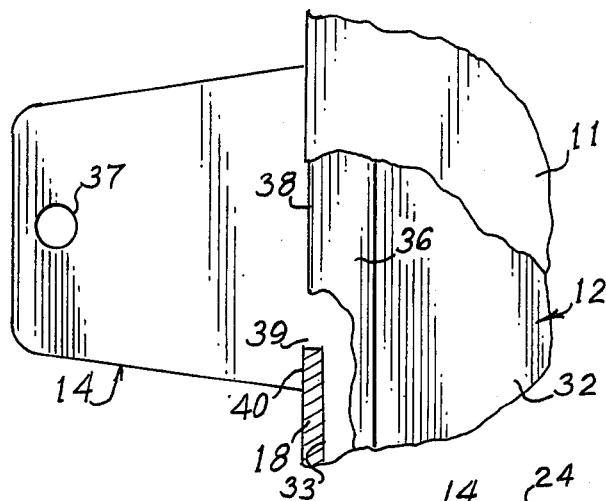
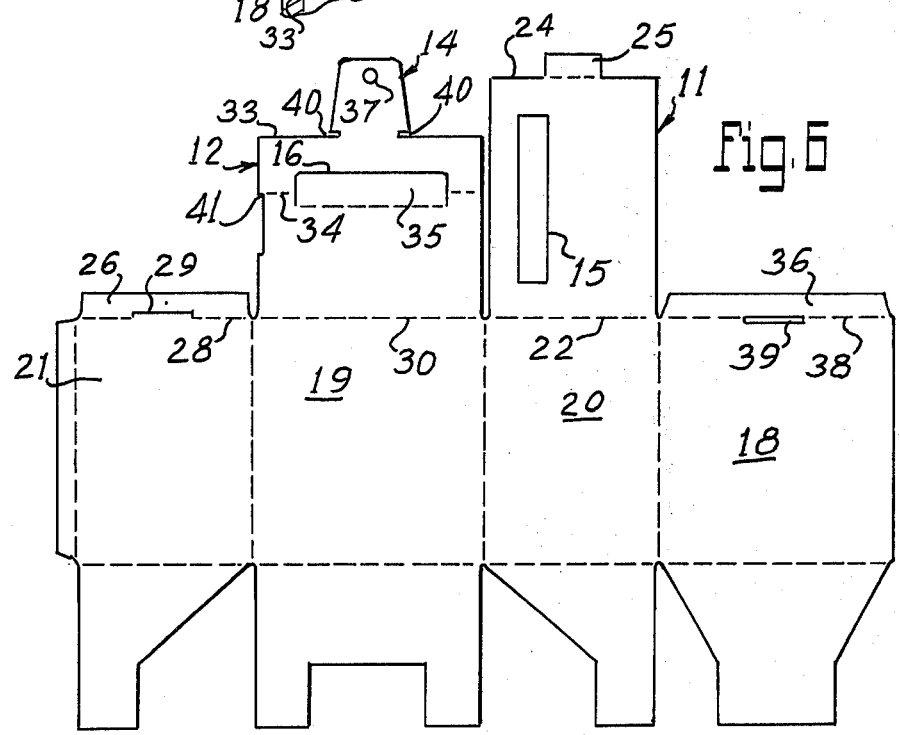

DISPOSABLE RECEPTABLE FOR EXPENDABLE ITEM

FIELD OF THE INVENTION

This invention relates generally to receptacles for expendable items, and is more particularly concerned with a lockable, disposable receptacle for hypodermic needles and syringes and similar expendable items.

BACKGROUND OF THE INVENTION

The use of expendable, or disposable, one-time-use equipment has become quite common in the medical field. Such equipment and supplies are highly desirable because they are packaged in a sterile condition, and remain so packaged until just before use. This removes the necessity for disassembling equipment for autoclaving and reassembling equipment after it is sterile.

In the case of hypodermic needles and syringes, it has become common practice to provide a syringe with a needle attached, the entire device being packaged in a sterile condition to be used one time and disposed of. Further, some syringes are sold with a given quantity of a medicament so that the needle and syringe are used one time and disposed of. It will of course be realized that a used hypodermic needle is contaminated, and should be disposed of in such a manner that no one will inadvertently engage the sharp point. When disposable hypodermic needles are used in large quantities, the problem of safe disposal becomes acute.

In the past, various containers have been utilized for disposal of used hypodermic needles with the attached syringes. These containers have generally been left open while used items are to be placed within the container; then, a cover has been provided to cover the container for disposal. Such containers have been hazardous, however, because a person placing a syringe or other item into the container exposes his hand to numerous needles that have been previously placed into the container. Also, when one syringe is dropped into the container, other syringes with their attached needles may be displaced upwardly and may engage a person's hand. While the pricking of the needle may be only slightly uncomfortable, it will be understood that the primary objection is the danger of infection or other damage from the needles contaminated with germs or various medicines and the like. One attept to remedy the hazardous situation has been to utilize a needle cutter whereby the needle is severed from the syringe. Though this cutting may render the syringe relatively harmless, the cutting itself has been hazardous, frequently spattering the area with blood or other contents of a syringe. Furthermore, when the cutter becomes dull, it is very difficult to sever the needle from the syringe, and a person may be injured during this operation.

SUMMARY OF THE INVENTION

The present invention overcomes the above mentioned and other difficulties with the prior art receptacles by providing a container for receiving used medical items and the like, the container including a first baffle disposed thereover and defining a first item-receiving opening, and a second baffle disposed thereover and defining a second item-receiving opening. The first and second item-receiving openings are horizontally displaced from each other. The second baffle can assume a receiving position wherein the first and second item-receiving openings are vertically displaced to allow items to pass through both openings and be received by the container, and a closed position wherein each baffle effectively closes the item-receiving opening in the other baffle. A locking tab secures the second baffle in the closed position, and it is contemplated that the entire receptacle will be disposable, as by incineration.

BRIEF DESCRIPTION OF THE DRAWINGS

These and other features and advantages of the present invention will become apparent from the consideration of the following specification when taken in conjunction with the accompanying drawings in which:

FIG. 4 is a view similar to FIG. 3 showing the baffles in closed position;

FIG. 5 is an enlarged detail view showing the locking means for the baffle; and, FIG. 6 is a plan view showing the blank for forming the receptacle disclosed in FIGS. 1-5.

DESCRIPTION OF AN EMBODIMENT OF THE INVENTION

Referring now more particularly to the drawings, and to that embodiment of the invention here chosen by way of illustration, it will be seen that the receptacle is a generally rectangular box or container 10 having four walls, and a top formed by the two baffles 11 and 12. A tab 14 extends from the front of the box, and the item-receiving openings 15 and 16 can be seen.

Figure 2:
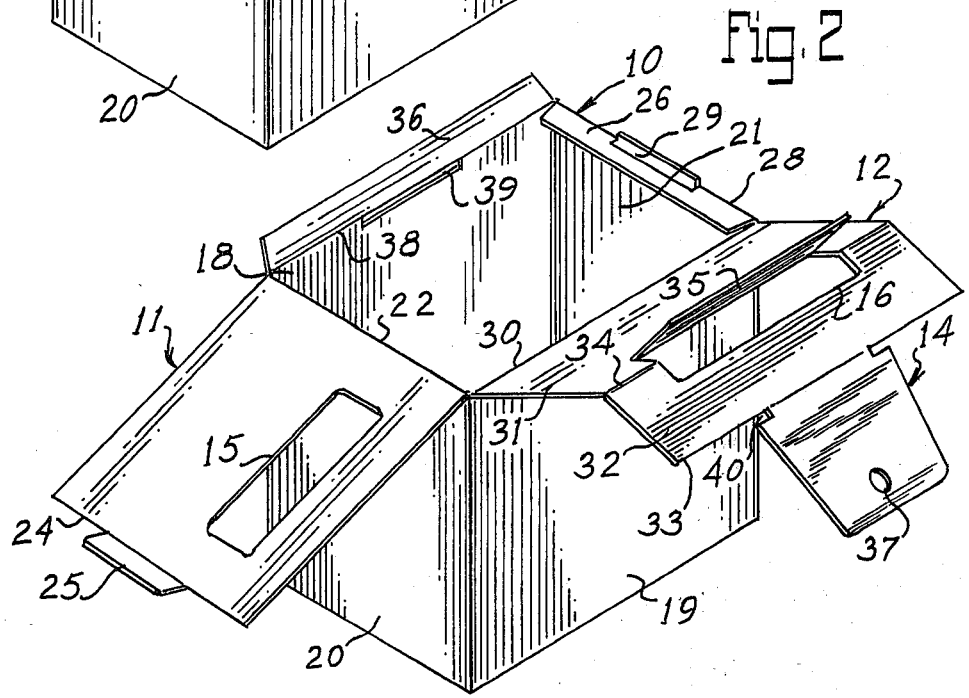
FIG. 2 is a perspective view of the receptacle shown in FIG. 1, the top flaps being opened to show their configurations.

Attention is directed to FIG. 2 of the drawings for an understanding of the construction of the receptacle of the present invention. Here it will be seen that the container 10 comprises the four walls including a front panel 18, a back 19, and side panels 20 and 21.

Figure 1:
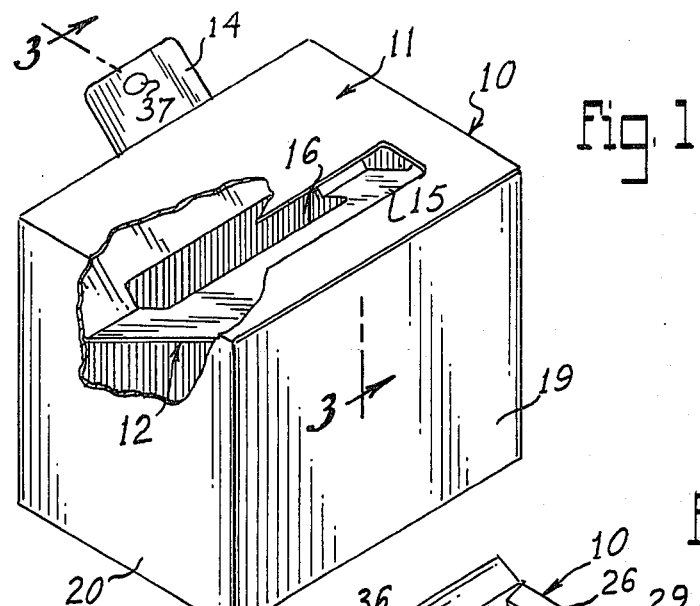
FIG. 1 is a perspective view of a receptacle made in accordance with the present invention, a portion being broken away to show the internal arrangement.

The side panel 20 carries the baffle 11 at its upper edge, the two being joined along the fold line 22. The extending edge 24 of the baffle 11 is provided with a tab 25 for holding the baffle 11 in place when the receptacle is closed, as shown in FIG. 1 of the drawings.

The opposite side panel 21 carries a flange 26 at its upper edge. The flange 26 is connected to the side panel 21 along a fold line 28, and there is a slot 29 in the flange 24 substantially at the fold line 28. Thus, the baffle 11 can be folded over the top of the container 10, hinging along the fold line 22; and, with the flange 26 folded inwardly as shown in FIG. 2, the slot 29 will be appropriately placed to receive the tab 25 therethrough.

The rear, or back, panel 19 carries the baffle 12 at its upper edge, the baffle 12 being hinged along the fold line 30. The baffle 12 is divided into two sections 31 and 32 which are disposable in different planes due to the presence of a fold line 34 which extends along the baffle 12, parallel to the fold line 30. The tab 14 is carried by the extending end 33 of the baffle 12, and this tab will be discussed in more detail hereinafter.

Generally along the fold line 34, there is an opening 16 which constitutes the item-receiving opening 16 discussed in connection with FIG. 1 of the drawings. It should be noticed that the opening 16 is formed by cutting along three sides, and only scoring the fourth side, to leave a flap 35.

On the front panel 18, there is a flange 36 connected to the front panel 18 along a fold line 38. A slot 39 is cut into the panel 18 contiguous with the fold line 38 and generally centrally thereof. It will therefore be seen that the baffle 12 is hinged along the fold line 30 to be disposed over the open top of the container 10, and the tab 14 can be received through the slot 39. The tab 14 will fit snugly within the slot 39 to be held in a given position.

Figure 3:
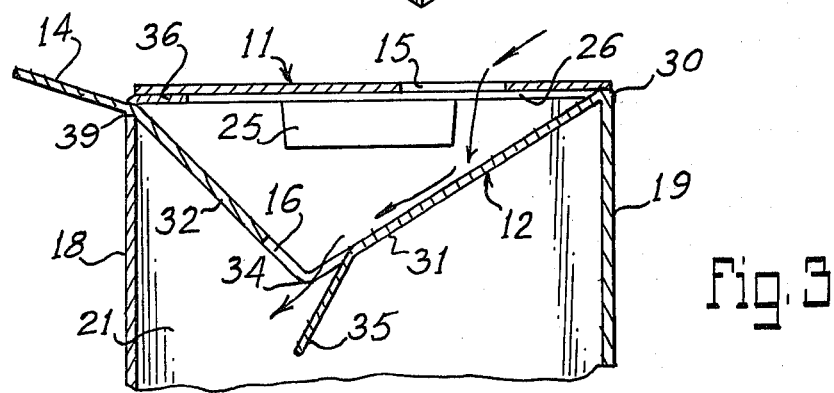
FIG. 3 is a cross-sectional view taken substantially along the line 3—3 in FIG. 1, showing the baffles in open position.

With the foregoing description in mind, attention is directed to FIG. 3 of the drawings for an understanding of the operation of the device. It should now be understood that the baffle 12 will be folded over the open top of the container 10, and the tab 14 will be inserted through the slot 39. Due to the presence of the fold line 34, the baffle 12 will assume a position wherein the section 31 slopes downwardly from the fold line 30, then upwardly from the fold line 34. At the fold line 34, the opening 16 is placed with the flap 35 extending downwardly into the container 10 from one edge of the opening 16. It will be seen that the tab 14 is long enough that the opening 16 can be placed well below tha top edge of the container 10, and the slot 39 acts as a holding means to retain the desired position of the tab 14.

With the baffle 12 in place, the flange 36 is folded inwardly and the baffle 11 is folded over the baffle 12. The upper edge of the rear wall 19 and the flange 36 will support the two edges of the baffle 11, and the tab 25 will be received within the slot 29, the extending edge 24 of the baffle 11 resting on the flange 26. This construction will provide a sufficient closure for the container 10. It will be obvious that additional taping, stapling or the like may be utilized for further security if desired.

With the container 10 so closed, and continuing to look at FIG. 3 of the drawings, it will be seen that an item can be placed through the opening 15 as shown by the arrows, and the item will pass through the opening 15 and engage the section 31 of the baffle 12. Since the section 31 is sloped downwardly, an item will roll by gravity towards the fold line 34 where the item will pass through the opening 16 and into the container 10. Since the opening 15 is laterally off-set from the opening 16, a person will not engage other items, even if he places his hand immediately adjacent to the opening 15 at the time of making the deposit. Even in the unlikely event that an item bounces upwardly through the opening 16, the item could not move sideways to pass through the opening 15 also.

It will therefore be seen that the receptacle of the present invention can be used for many relatively hazardous items such as hypodermic needles with syringes, and there is no need to remove the needle from the syringe before depositing the item into the receptacle. A syringe with the attached needle can simply be dropped through the opening 15, and the item will pass through the displaced opening 16 and pass into the container 10.

Attention is next directed to FIGS. 4 and 5 of the drawings for an understanding of the closing and locking of the receptacle of the present invention. From the foregoing, it will be understood that the tab 14 can be pulled through the slot 39, using the hole 37 as a grip, to cause the baffle 12 to assume a position generally along the top of the container 10. This position is shown in FIG. 4 of the drawings where it will be seen that the tab 14 has been pulled out to its greatest extent so that the baffle 12 assumes a position generally parallel to the baffle 11. It will be understood that, as shown in the drawings, the flange 36 is between the baffle 12 and the baffle 11, causing a signficant slope to the baffle 12; however, the thickness of the material is exaggerated for purposes of illustration, and any slope, or space between the baffles, would be negligible in actual practice. It will therefore be seen in FIG. 4 of the drawings that the opening 16 is closely adjacent to the baffle 11, and horizontally displaced from the opening 15. The result is that no item within the container 10 can pass through the opening 16 so long as the tab 14 is pulled outwardly, and the baffle 12 is adjacent to the baffle 11.

To maintain the tab 14 in its outermost position, the tab is constructed to be of increasing width from its outer end towards the baffle 12. The tab 14 then has a constricted portion so that the tab 14 defines a pair of notches 40. It will therefore be seen that, when the tab 14 is pulled outwardly, the tab will somewhat crowd its way through the slot 39; then, when the notches 40 reach the slot 39, the tab 14 will expand to its normal size and the front wall 18 will be inserted into the notches 40. This will provide a sufficient lock to prevent the return of the tab 14. As a result, the baffle 12 must maintain the position shown in FIG. 4 of the drawings.

It will be understood by those skilled in the art that the receptacle shown in FIGS. 1–5, and as discussed above, may be made of numerous materials and by numerous techniques. It is contemplated, however, that the receptacle will be constructed of, for example, corrugated fiberboard which can be cut and formed by conventional techniques. One blank for making a receptacle is shown in FIG. 6 of the drawings. In FIG. 6, the fully cut lines are shown by solid lines, and the scored lines are shown by broken lines. The reference numerals previously applied to various portions of the receptacle are applied to the blank shown in FIG. 6 of the drawings, and very little explanation will be required for an understanding of the blank.

It will be noted that, on the baffle 12, there is a notch 41. This notch 41 is provided so that the tab 25 on the baffle 11 will have sufficient clearance when the baffle 12 is in the closed and locked position as shown in FIG. 4.

It will also be seen that the blank shown in FIG. 6 includes a foldable bottom of a conventional design such that the bottom does not have to be taped, stapled or the like, but will lock sufficiently with proper folding. Again, those skilled in the art will be familiar with the arrangement shown and no further description is deemed necessary. It should of course be understood that other forms of bottom for the receptacle are equally contemplated by the present invention, the only requirement being that some form of bottom closure be provided. It will also be understood that numerous other materials may be used, the particular material being selected to prevent damage or hazard depending on the proposed contents of the receptacle.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as defined in the appended claims.

I claim:

1. A receptacle for receiving expendable items, said receptacle including a container, a first baffle generally closing the top of said container and defining a first opening through said first baffle of such size and shape to receive said expendable items therethrough, a second baffle disposed below said first baffle, said second baffle defining a second opening therethrough of such size and shape to receive said expendable items, said second opening being horizontally displaced from said first opening, said first baffle and said second baffle defining a space therebetween sufficient to allow said expendable items to pass through said first opening, between said first baffle and said second baffle, and through said second opening to be received within said container.

2. A receptacle as claimed in claim 1, said second baffle having a first fold line for defining a first section of said second baffle and a second section of said second baffle, said second opening being located generally along said first fold line, said first section of said second baffle being generally beneath said first opening and slanted for directing said expendable items towards said second opening.

3. A receptacle as claimed in claim 2, said first section of said second baffle being hinged with respect to said container along a second fold line generally at the top of said container, and further including a tab fixed to said second section of said second baffle for holding said second baffle spaced below said first baffle.

4. A receptacle as claimed in claim 3, said second fold line being generally at one edge of said first baffle and parallel thereto, holding means for said tab generally at the opposite edge of said first baffle, said holding means for said tab comprising a slot defined in said container.

5. A receptacle as claimed in claim 4, said second baffle being movable about said second fold line to a position generally parallel to said first baffle so that said first baffle effectively closes said second opening and said second baffle effectively closes said first opening, and further including locking means for locking said tab when said second baffle is parallel to said first baffle.

6. A receptacle as claimed in claim 5, said tab defining at least one notch adjacent to said second section of said second baffle, said notch receiving an edge of said slot to constitute said locking means.

* * * * *